(12) United States Patent
Twomey et al.

(10) Patent No.: US 10,405,874 B2
(45) Date of Patent: Sep. 10, 2019

(54) SURGICAL INSTRUMENT

(71) Applicant: COVIDIEN LP, Mansfield, MA (US)

(72) Inventors: John R. Twomey, Superior, CO (US); Jessica E. C. Olson, Frederick, CO (US); Grant T. Sims, Littleton, CO (US); Loren Toth, Lakewood, CO (US); Monte S. Fry, Longmont, CO (US); Michael B. Lyons, Boulder, CO (US)

(73) Assignee: COVIDIEN LP, Mansfield, MA (US)

( * ) Notice: Subject to any disclaimer, the term of this patent is extended or adjusted under 35 U.S.C. 154(b) by 1319 days.

(21) Appl. No.: 14/268,140

(22) Filed: May 2, 2014

(65) Prior Publication Data

US 2015/0051640 A1 Feb. 19, 2015

Related U.S. Application Data

(60) Provisional application No. 61/865,443, filed on Aug. 13, 2013.

(51) Int. Cl.
*A61B 17/28* (2006.01)
*A61B 18/14* (2006.01)
(Continued)

(52) U.S. Cl.
CPC ...... *A61B 17/2833* (2013.01); *A61B 17/2841* (2013.01); *A61B 18/1445* (2013.01);
(Continued)

(58) Field of Classification Search
CPC .............. A61B 17/068–07292; A61B 2017/0688–07285; A61B 17/29;
(Continued)

(56) References Cited

U.S. PATENT DOCUMENTS 2,652,832 A * 9/1953 Castroviejo .......... A61B 17/062
606/147
D249,549 S 9/1978 Pike
(Continued)

FOREIGN PATENT DOCUMENTS

CN 201299462 9/2009
DE 2415263 A1 10/1975
(Continued)

OTHER PUBLICATIONS

European Search Report dated Oct. 2, 2014 issued in European Appln No. 14180638.
(Continued)

*Primary Examiner* — Jonathan A Hollm

(57) ABSTRACT

A surgical instrument is provided. The surgical instrument includes a housing. A movable handle is coupled to the housing and is configured to approximate a pair of jaw members toward and away from one another. A latch mechanism operably couples to the movable handle and includes one or more mechanical interfaces configured to selectively engage a corresponding mechanical interface disposed within the housing to lock and unlock the jaw members in an approximated configuration. When the movable handle is in a jammed position, the mechanical interface(s) of the latch mechanism is/are configured to deform and separate from the corresponding mechanical interface disposed within the housing when the movable handle is moved from the jammed position.

20 Claims, 6 Drawing Sheets

(51) Int. Cl.
   *A61B 34/00* (2016.01)
   *A61B 18/00* (2006.01)
   *A61B 90/00* (2016.01)

(52) U.S. Cl.
   CPC ...... *A61B 34/76* (2016.02); *A61B 2017/2845* (2013.01); *A61B 2018/0063* (2013.01); *A61B 2018/00791* (2013.01); *A61B 2018/00875* (2013.01); *A61B 2018/1455* (2013.01); *A61B 2090/065* (2016.02)

(58) Field of Classification Search
   CPC ........... A61B 17/2909; A61B 2017/291–2925; A61B 17/28; A61B 17/2833–2841; A61B 2017/2837–2845
   See application file for complete search history.

(56) References Cited

U.S. PATENT DOCUMENTS

| | | |
|---|---|---|
| D263,020 S | 2/1982 | Rau, III |
| D295,893 S | 5/1988 | Sharkany et al. |
| D295,894 S | 5/1988 | Sharkany et al. |
| 4,753,235 A | 6/1988 | Hasson |
| D298,353 S | 11/1988 | Manno |
| D299,413 S | 1/1989 | DeCarolis |
| 4,823,792 A * | 4/1989 | Dulebohn .......... A61B 17/2812 294/99.2 |
| 5,026,370 A | 6/1991 | Lottick |
| 5,104,397 A * | 4/1992 | Vasconcelos ............. B25B 7/14 606/206 |
| 5,176,702 A * | 1/1993 | Bales ................. A61B 17/2909 600/564 |
| D343,453 S | 1/1994 | Noda |
| D348,930 S | 7/1994 | Olson |
| D349,341 S | 8/1994 | Lichtman et al. |
| D354,564 S | 1/1995 | Medema |
| D358,887 S | 5/1995 | Feinberg |
| 5,425,743 A | 6/1995 | Nicholas |
| D384,413 S | 9/1997 | Zlock et al. |
| 5,730,740 A * | 3/1998 | Wales ................. A61B 17/2909 606/1 |
| H1745 H | 4/1998 | Paraschac |
| D402,028 S | 12/1998 | Grimm et al. |
| D408,018 S | 4/1999 | McNaughton |
| D416,089 S | 11/1999 | Barton et al. |
| D424,694 S | 5/2000 | Tetzlaff et al. |
| D425,201 S | 5/2000 | Tetzlaff et al. |
| H1904 H | 10/2000 | Yates et al. |
| D449,886 S | 10/2001 | Tetzlaff et al. |
| D453,923 S | 2/2002 | Olson |
| D454,951 S | 3/2002 | Bon |
| D457,958 S | 5/2002 | Dycus et al. |
| D457,959 S | 5/2002 | Tetzlaff et al. |
| H2037 H | 7/2002 | Yates et al. |
| D465,281 S | 11/2002 | Lang |
| D466,209 S | 11/2002 | Bon |
| D493,888 S | 8/2004 | Reschke |
| D496,997 S | 10/2004 | Dycus et al. |
| D499,181 S | 11/2004 | Dycus et al. |
| D502,994 S | 3/2005 | Blake, III |
| D509,297 S | 9/2005 | Wells |
| D525,361 S | 7/2006 | Hushka |
| D531,311 S | 10/2006 | Guerra et al. |
| D533,274 S | 12/2006 | Visconti et al. |
| D533,942 S | 12/2006 | Kerr et al. |
| D535,027 S | 1/2007 | James et al. |
| 7,160,299 B2 | 1/2007 | Baily |
| D538,932 S | 3/2007 | Malik |
| D541,418 S | 4/2007 | Schechter et al. |
| D541,611 S | 5/2007 | Aglassinger |
| D541,938 S | 5/2007 | Kerr et al. |
| D545,432 S | 6/2007 | Watanabe |
| D547,154 S | 7/2007 | Lee |
| D564,662 S | 3/2008 | Moses et al. |
| D567,943 S | 4/2008 | Moses et al. |
| D575,395 S | 8/2008 | Hushka |
| D575,401 S | 8/2008 | Hixson et al. |
| D582,038 S | 12/2008 | Swoyer et al. |
| D617,900 S | 6/2010 | Kingsley et al. |
| D617,901 S | 6/2010 | Unger et al. |
| D617,902 S | 6/2010 | Twomey et al. |
| D617,903 S | 6/2010 | Unger et al. |
| D618,798 S | 6/2010 | Olson et al. |
| D621,503 S | 8/2010 | Otten et al. |
| 7,766,910 B2 | 8/2010 | Hixson et al. |
| D627,462 S | 11/2010 | Kingsley |
| D628,289 S | 11/2010 | Romero |
| D628,290 S | 11/2010 | Romero |
| D630,324 S | 1/2011 | Reschke |
| D649,249 S | 11/2011 | Guerra |
| D649,643 S | 11/2011 | Allen, IV et al. |
| D661,394 S | 6/2012 | Romero et al. |
| D670,808 S | 11/2012 | Moua et al. |
| D680,220 S | 4/2013 | Rachlin |
| 2003/0018331 A1 | 1/2003 | Dycus et al. |
| 2004/0167569 A1 | 8/2004 | Dicesare et al. |
| 2007/0043352 A1 | 2/2007 | Garrison et al. |
| 2007/0175952 A1 * | 8/2007 | Shelton, IV ..... A61B 17/07207 227/176.1 |
| 2010/0228235 A1 | 9/2010 | Lee et al. |
| 2012/0215134 A1 | 8/2012 | Hunter-Jones et al. |
| 2012/0283727 A1 | 11/2012 | Twomey |

FOREIGN PATENT DOCUMENTS

| | | |
|---|---|---|
| DE | 02514501 A1 | 10/1976 |
| DE | 2627679 A1 | 1/1977 |
| DE | 03423356 C2 | 6/1986 |
| DE | 03612646 A1 | 4/1987 |
| DE | 3627221 A1 | 2/1988 |
| DE | 8712328 U1 | 2/1988 |
| DE | 04303882 C2 | 2/1995 |
| DE | 04403252 A1 | 8/1995 |
| DE | 19515914 C1 | 7/1996 |
| DE | 19506363 A1 | 8/1996 |
| DE | 29616210 U1 | 11/1996 |
| DE | 19608716 C1 | 4/1997 |
| DE | 19751106 A1 | 5/1998 |
| DE | 19751108 A1 | 5/1999 |
| DE | 19946527 C1 | 7/2001 |
| DE | 20121161 U1 | 4/2002 |
| DE | 10045375 C2 | 10/2002 |
| DE | 202007009165 U1 | 8/2007 |
| DE | 202007009317 U1 | 8/2007 |
| DE | 202007009318 U1 | 8/2007 |
| DE | 10031773 B4 | 11/2007 |
| DE | 202007016233 U1 | 1/2008 |
| DE | 19738457 B4 | 1/2009 |
| DE | 102004026179 B4 | 1/2009 |
| DE | 102008018406 B3 | 7/2009 |
| EP | 1281878 A1 | 2/2003 |
| EP | 1159926 A3 | 3/2003 |
| JP | 61-501068 | 9/1984 |
| JP | 10-24051 A | 1/1989 |
| JP | 11-47150 A | 6/1989 |
| JP | 6-502328 | 3/1992 |
| JP | 5-5106 | 1/1993 |
| JP | 05-40112 | 2/1993 |
| JP | 0006030945 A | 2/1994 |
| JP | 6-121797 A | 5/1994 |
| JP | 6-285078 A | 10/1994 |
| JP | 6-511401 | 12/1994 |
| JP | 06343644 A | 12/1994 |
| JP | 07265328 A | 10/1995 |
| JP | 8-56955 | 5/1996 |
| JP | 08252263 A | 10/1996 |
| JP | 8-289895 A | 11/1996 |
| JP | 8-317934 A | 12/1996 |
| JP | 8-317936 A | 12/1996 |
| JP | 9-10223 C | 1/1997 |
| JP | 09000538 A | 1/1997 |
| JP | 9-122138 A | 5/1997 |
| JP | 0010000195 A | 1/1998 |

(56) References Cited

FOREIGN PATENT DOCUMENTS

| | | | |
|---|---|---|---|
| JP | 10-155798 A | 6/1998 |
| JP | 11-47149 | 2/1999 |
| JP | 11-070124 A | 3/1999 |
| JP | 11-169381 A | 6/1999 |
| JP | 11-192238 A | 7/1999 |
| JP | 11244298 A | 9/1999 |
| JP | 2000-102545 A | 4/2000 |
| JP | 2000-135222 A | 5/2000 |
| JP | 2000342599 A | 12/2000 |
| JP | 2000350732 A | 12/2000 |
| JP | 2001008944 A | 1/2001 |
| JP | 2001-29355 | 2/2001 |
| JP | 2001029356 A | 2/2001 |
| JP | 2001-03400 | 4/2001 |
| JP | 2001128990 A | 5/2001 |
| JP | 2001-190564 A | 7/2001 |
| JP | 2002-136525 A | 5/2002 |
| JP | 2002-528166 A | 9/2002 |
| JP | 2003-116871 A | 4/2003 |
| JP | 2003-175052 A | 6/2003 |
| JP | 2003245285 A | 9/2003 |
| JP | 2004-517668 A | 6/2004 |
| JP | 2004-528869 A | 9/2004 |
| JP | 2005-152663 A | 6/2005 |
| JP | 2005-253789 A | 9/2005 |
| JP | 2005312807 A | 11/2005 |
| JP | 2006-015078 A | 1/2006 |
| JP | 2006-501939 A | 1/2006 |
| JP | 2006-095316 A | 4/2006 |
| JP | 2008-054926 A | 3/2008 |
| JP | 2011125195 A | 6/2011 |
| SU | 401367 A1 | 11/1974 |
| WO | 0036986 A1 | 6/2000 |
| WO | 0059392 A1 | 10/2000 |
| WO | 0115614 A1 | 3/2001 |
| WO | 0154604 A1 | 8/2001 |
| WO | 0245589 A3 | 9/2002 |
| WO | 06/021269 A1 | 3/2006 |
| WO | 05110264 A3 | 4/2006 |
| WO | 08/040483 A1 | 4/2008 |
| WO | 2011/018154 A1 | 2/2011 |

OTHER PUBLICATIONS

U.S. Appl. No. 13/731,674, filed Dec. 31, 2012; inventor: Siebrecht.
U.S. Appl. No. 14/065,644, filed Oct. 29, 2013; inventor: Reschke.
U.S. Appl. No. 14/098,953, filed Dec. 6, 2013; inventor: Cunningham.
U.S. Appl. No. 14/100,237, filed Dec. 9, 2013; inventor: Reschke.
U.S. Appl. No. 14/103,971, filed Dec. 12, 2013; inventor: Roy.
U.S. Appl. No. 14/105,374, filed Dec. 13, 2013; inventor: Moua.
U.S. Appl. No. 14/152,618, filed Jan. 10, 2014; inventor: Artale.
U.S. Appl. No. 14/152,690. filed Jan. 10, 2014; inventor: Hart.
U.S. Appl. No. 14/169,358, filed Jan. 31, 2014; inventor: Reschke.
U.S. Appl. No. 14/173,391. filed Feb. 5, 2014; inventor: Kharin.
U.S. Appl. No. 14/176,341, filed Feb. 10, 2014; inventor: Hart.
U.S. Appl. No. 14/177,812, filed Feb. 11, 2014; inventor: Dycus.
U.S. Appl. No. 14/182,894, filed Feb. 18, 2014; inventor: Hart.
U.S. Appl. No. 14/182,967, filed Feb. 18, 2014; inventor: Latimer.
U.S. Appl. No. 14/183,090, filed Feb. 18, 2014; inventor: Arts.
U.S. Appl. No. 14/196,066, filed Mar. 4, 2014; inventor: McCullough.
U.S. Appl. No. 14/250,180, filed Apr. 10, 2014; inventor: Guerra.
U.S. Appl. No. 14/253,017, filed Apr. 15, 2014; inventor: Orszulak.
U.S. Appl. No. 14/260,905, filed Apr. 24, 2014; inventor: Jensen.
U.S. Appl. No. 14/268,051, filed May 2, 2014; inventor: Hart.
U.S. Appl. No. 14/268,140, filed May 2, 2014; inventor: Twomey.
U.S. Appl. No. 14/273,350, filed May 8, 2014; inventor: Gilbert.
U.S. Appl. No. 14/274,445, filed May 9, 2014; inventor: Hixson.
U.S. Appl. No. 14/276,465, filed May 13, 2014; inventor: Kappus.
U.S. Appl. No. 14/282,738, filed May 20, 2014; inventor: Rachlin.
U.S. Appl. No. 14/284,618, filed May 22, 2014; inventor: Hempstead.
U.S. Appl. No. 14/286,105, filed May 23, 2014; inventor: Johnson.
U.S. Appl. No. 14/294,316, filed Jun. 3, 2014; inventor: Johnson.
U.S. Appl. No. 14/295,049, filed Jun. 3, 2014; inventor: Couture.
U.S. Appl. No. 14/295,730, filed Jun. 4, 2014; inventor: Sartor.
U.S. Appl. No. 14/295,757, filed Jun. 4, 2014; inventor: McKenna.
U.S. Appl. No. 14/297,316, filed Jun. 5, 2014; inventor: Ackley.
U.S. Appl. No. 14/297,404, filed Jun. 5, 2014; inventor: Allen.
U.S. Appl. No. 14/299,740, filed Jun. 9, 2014; inventor: Larson.
U.S. Appl. No. 14/319,869, filed Jun. 30, 2014; inventor: Cunningham.
U.S. Appl. No. 14/322,513, filed Jul. 2, 2014; inventor: Duffin.
U.S. Appl. No. 14/335,303, filed Jul. 18, 2014; inventor: Lee.
Michael Choti, "Abdominoperineal Resection with the LigaSure Vessel Sealing System and LigaSure Atlas 20 cm Open Instrument" ; Innovations That Work, Jun. 2003.
Chung et al., "Clinical Experience of Sutureless Closed Hennorrhoidectomy with LigaSure" Diseases of the Colon & Rectum vol. 46, No. 1 Jan. 2003.
Tinkcler L.F., "Combined Diathermy and Suction Forceps" , Feb. 6, 1967 (Feb. 6, 1965), British Medical Journal Feb. 6, 1976, vol. 1, nr. 5431 p. 361, ISSN: 0007-1447.
Carbonell et al., "Comparison of theGyrus PlasmaKinetic Sealer and the Valleylab LigaSure Device in the Hemostasis of Small, Medium, and Large-Sized Arteries" Carolinas Laparoscopic and Advanced Surgery Program, Carolinas Medical Center, Charlotte, NC; Date: Aug. 2003.
Peterson et al. "Comparison of Healing Process Following Ligation with Sutures and Bipolar Vessel Sealing" Surgical Technology International (2001).
"Electrosurgery: A Historical Overview" Innovations in Electrosurgery; Sales/Product Literature; Dec. 31, 2000.
Johnson et al. "Evaluation of a Bipolar Electrothermal Vessel Sealing Device in Hemorrhoidectomy" Sales/Product Literature; Jan. 2004.
E. David Crawford "Evaluation of a New Vessel Sealing Device in Urologic Cancer Surgery" Sales/Product Literature 2000.
Johnson et al. "Evaluation of the LigaSure Vessel Sealing System in Hemorrhoidectormy" American College of Surgeons (ACS) Clinicla Congress Poster (2000).
Muller et al., "Extended Left Hemicolectomy Using the LigaSure Vessel Sealing System" Innovations That Work, Sep. 1999.
Kennedy et al. "High-burst-strength, feedback-controlled bipolar vessel sealing" Surgical Endoscopy (1998) 12: 876-878.
Burdette et al. "In Vivo Probe Measurement Technique for Determining Dielectric Properties At VHF Through Microwave Frequencies", IEEE Transactions on Microwave Theory and Techniques, vol. MTT-28, No. 4, Apr. 1980 pp. 414-427.
Carus et al., "Initial Experience With the LigaSure Vessel Sealing System in Abdominal Surgery" Innovations That Work, Jun. 2002.
Heniford et al. "Initial Research and Clinical Results with an Electrothermal Bipolar Vessel Sealer" Oct. 1999.
Heniford et al. "Initial Results with an Electrothermal Bipolar Vessel Sealer" Surgical Endoscopy (2000) 15:799-801.
Herman et al., "Laparoscopic Intestinal Resection With the LigaSure Vessel Sealing System: A Case Report"; Innovations That Work, Feb. 2002.
Koyle et al., "Laparoscopic Palomo Varicocele Ligation in Children and Adolescents" Pediatric Endosurgery & Innovative Techniques, vol. 6, No. 1, 2002.
W. Scott Helton, "LigaSure Vessel Sealing System: Revolutionary Hemostasis Product for General Surgery"; Sales/Product Literature 1999.
LigaSure Vessel Sealing System, the Seal of Confidence in General, Gynecologic, Urologic, and Laparaoscopic Surgery; Sales/Product Literature; Apr. 2002.
Joseph Ortenberg "LigaSure System Used in Laparoscopic 1st and 2nd Stage Orchiopexy" Innovations That Work, Nov. 2002.
Sigel et al. "The Mechanism of Blood Vessel Closure by High Frequency Electrocoagulation" Surgery Gynecology & Obstetrics, Oct. 1965 pp. 823-831.
Sampayan et al, "Multilayer Ultra-High Gradient Insulator Technology" Discharges and Electrical Insulation in Vacuum, 1998. Netherlands Aug. 17-21, 1998; vol. 2, pp. 740-743.

(56) References Cited

OTHER PUBLICATIONS

Paul G. Horgan, "A Novel Technique for Parenchymal Division During Hepatectomy" The American Journal of Surgery, vol. 181, No. 3, Apr. 2001 pp. 236-237.
Benaron et al., "Optical Time-Of-Flight and Absorbance Imaging of Biologic Media", Science, American Association for the Advancement of Science, Washington, DC, vol. 259, Mar. 5, 1993, pp. 1463-1466.
Olsson et al. "Radical Cystectomy in Females" Current Surgical Techniques in Urology, vol. 14, Issue 3, 2001.
Palazzo et al. "Randomized clinical trial of Ligasure versus open haemorrhoidectomy" British Journal of Surgery 2002, 89, 154-157.
Levy et al. "Randomized Trial of Suture Versus Electrosurgical Bipolar Vessel Sealing in Vaginal hysterectomy" Obstetrics & Gynecology, vol. 102, No. 1, Jul. 2003.
"Reducing Needlestick Injuries in the Operating Room" Sales/Product Literature 2001.
Bergdahl et al. "Studies on Coagulation and the Development of an Automatic Computerized Bipolar Coagulator" J. Neurosurg, vol. 75, July 1991, pp. 148-151.
Strasberg et al. "A Phase I Study of the LigaSure Vessel Sealing System in Hepatic Surgery" Section of HPB Surger, Washington University School of Medicine, St. Louis MO, Presented at AHPBA, Feb. 2001.
Sayfan et al. "Sutureless Closed Hemorrhoidectomy: A New Technique" Annals of Surgery vol. 234 No. 1 Jul. 2001; pp. 21-24.
Levy et al., "Update on Hysterectomy—New Technologies and Techniques" OBG Management, Feb. 2003.
Dulemba et al. "Use of a Bipolar Electrothermal Vessel Sealer in Laparoscopically Assisted Vaginal Hysterectomy" Sales/Product Literature; Jan. 2004.
Strasberg et al., "Use of a Bipolar Vessel-Sealing Device for Parenchymal Transection During Liver Surgery" Journal of Gastrointestinal Surgery, vol. 6, No. 4, Jul./Aug. 2002 pp. 569-574.
Sengupta et al., "Use of a Computer-Controlled Bipolar Diathermy System in Radical Prostatectomies and Other Open Urological Surgery" ANZ Journal of Surgery (2001) 71.9 pp. 538-540.
Rothenberg et al. "Use of the LigaSure Vessel Sealing System in Minimally Invasive Surgery in Children" Int'l Pediatric Endosurgery Group (IPEG) 2000.
Crawford et al. "Use of the LigaSure Vessel Sealing System in Urologic Cancer Surgery" Grand Rounds in Urology 1999 vol. 1 Issue 4 pp. 10-17.
Craig Johnson, "Use of the LigaSure Vessel Sealing System in Bloodless Hemorrhoidectomy" Innovations That Work, Mar. 2000.
Levy et al. "Use of a New Energy-based Vessel Ligation Device During Vaginal Hysterectomy" Int'l Federation of Gynecology and Obstetrics (FIGO) World Congress 1999.
Barbara Levy, "Use of a New Vessel Ligation Device During Vaginal Hysterectomy" FIGO 2000, Washington, D.C.
E. David Crawford "Use of a Novel Vessel Sealing Technology in Management of the Dorsal Veinous Complex" Sales/Product Literature 2000.
Jarrett et al., "Use of the LigaSure Vessel Sealing System for Peri-Hilar Vessels in Laparoscopic Nephrectomy" Sales/ Product Literature 2000.
Crouch et al. "A Velocity-Dependent Model for Needle Insertion in Soft Tissue" MICCAI 2005; LNCS 3750 pp. 624-632, Dated: 2005.
McLellan et al. "Vessel Sealing for Hemostasis During Pelvic Surgery" Int'l Federation of Gynecology and Obstetrics FIGO World Congress 2000, Washington, D.C.
McLellan et al. "Vessel Sealing for Hemostasis During Gynecologic Surgery" Sales/Product Literature 1999.
U.S. Appl. No. 08/926,869, filed Sep. 10, 1997; inventor: James G. Chandler.
U.S. Appl. No. 09/177,950, filed Oct. 23, 1998; inventor: Randel A. Frazier.
U.S. Appl. No. 09/387,883, filed Sep. 1, 1999; inventor: Dale F. Schmaltz.
U.S. Appl. No. 09/591,328, filed Jun. 9, 2000; inventor: Thomas P. Ryan.
U.S. Appl. No. 12/336,970, filed Dec. 17, 2008; inventor: Paul R. Sremeich.
European Office Action dated May 17, 2017 issued in EP Application No. 14 180 638.

\* cited by examiner

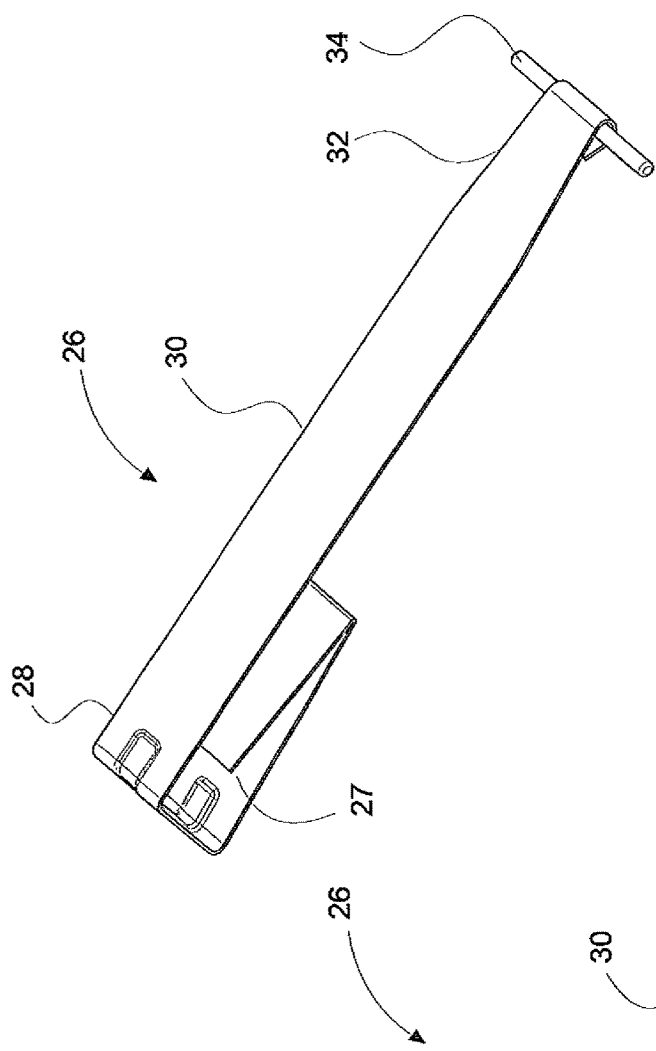
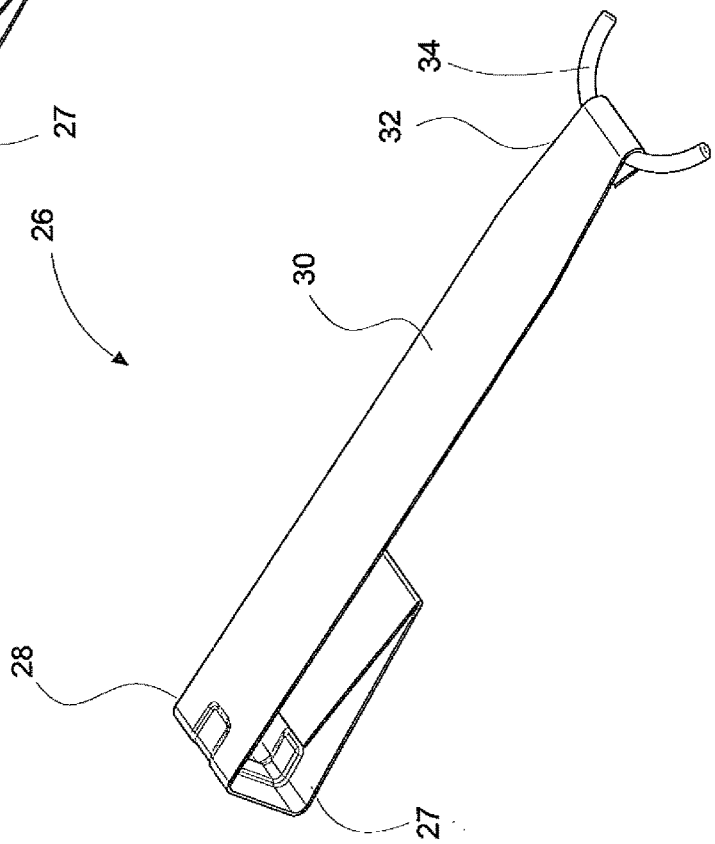
Fig. 4A
Fig. 4B

SURGICAL INSTRUMENT

CROSS REFERENCE TO RELATED APPLICATION

The present application claims the benefit of and priority to U.S. Provisional Application Ser. No. 61/865,443, filed on Aug. 13, 2013, the entire contents of which are incorporated herein by reference.

BACKGROUND

1. Technical Field

The present disclosure relates to surgical instruments. In particular, the present disclosure relates to a surgical instrument that includes a fail safe latch mechanism.

2. Background of Related Art

Instruments such as electrosurgical forceps are commonly used in open and endoscopic surgical procedures to coagulate, cauterize and seal tissue. Such forceps typically include a pair of jaws that can be controlled by a surgeon to grasp targeted tissue, such as, e.g., a blood vessel. Utilizing a movable handle of the forceps the jaws may be approximated toward one another to apply a mechanical clamping force to the tissue. The jaws are associated with at least one electrode to permit the delivery of electrosurgical energy to the tissue. The combination of the mechanical clamping force and the electrosurgical energy has been demonstrated to join adjacent layers of tissue captured between the jaws.

A latching or locking mechanism may be a component of the forceps and utilized to temporarily lock the movable handle in a proximal position against the bias of a spring (or the like) to clamp the jaws on the tissue. As can be appreciated, if the latch mechanism were to fail during use (e.g., get jammed, trapped or stuck into a locked configuration), for example, while the jaws were clamped on tissue, it could prove difficult to remove the jaws and/or the forceps safely from the surgical site.

SUMMARY

A surgical instrument that includes a fail safe latch mechanism may prove useful in the surgical arena.

Aspects of the present disclosure are described in detail with reference to the drawing figures wherein like reference numerals identify similar or identical elements. As used herein, the term "distal" refers to the portion that is being described which is further from a user, while the term "proximal" refers to the portion that is being described which is closer to a user.

An aspect of the instant disclosure provides a surgical instrument including a housing and a movable handle coupled to the housing. The movable handle is configured to approximate a pair of jaw members toward and away from one another. A latch mechanism operably couples to the movable handle and includes one or more mechanical interfaces configured to releasably engage a corresponding mechanical interface disposed within the housing for locking and unlocking the jaw members in and from an approximated configuration. When the movable handle is in a jammed position, the mechanical interface(s) of latch mechanism is/are configured deform and separate from the corresponding mechanical interface disposed within the housing when the movable handle is moved distally from the jammed position. The latch mechanism may be formed from metal.

The latch mechanism may include a distal end that couples to the movable handle, a generally elongated medial portion, and a proximal end that supports the mechanical interface(s) of the latch mechanism. The mechanical interface(s) of the latch mechanism may be a latch pin that extends perpendicularly with respect to the generally elongated medial portion of the latch mechanism and the corresponding mechanical interface disposed within the housing may be in the form of a railway. The latch pin may extend from a left or right side of the generally elongated medial portion. Alternatively, the latch pin may extend from left and right sides of the generally elongated medial portion.

The generally elongated medial portion may be tapered at the proximal end of the latch mechanism to facilitate deformation thereof. The generally elongated medial portion may include a notch at the proximal end of the latch mechanism to facilitate deformation thereof. The mechanical interface(s) of the latch mechanism may remain coupled to the proximal end of the latch mechanism when the mechanical interface(s) is/are deformed to un-latch the corresponding mechanical interface disposed within the housing. The mechanical interface(s) of the latch mechanism may be configured to deform and separate from the corresponding mechanical interface disposed within the housing when the movable handle is moved distally from the jammed position with a predetermined force ranging from about 29 ft·lb to about 31 ft·lb.

An aspect of the instant disclosure provides a surgical instrument. The surgical instrument includes a housing. A movable handle is coupled to the housing and is configured to approximate a pair of jaw members of the surgical instrument toward one another when the movable handle is moved proximally. A latch mechanism includes a distal end that couples to the movable handle and a proximal end that supports one or more mechanical interfaces configured to releasably engage a corresponding mechanical interface disposed within a stationary handle of the housing. The latch mechanism includes a generally elongated medial portion that extends from the distal end thereof. The mechanical interface of the latch mechanism engages the mechanical interface disposed within the stationary handle to lock and unlock the jaw members in and from an approximated configuration when the movable handle is moved. The at least one mechanical interface of the latch mechanism is configured to deform and separate from the corresponding mechanical interface disposed within the stationary handle when the movable handle is moved from a jammed position within the stationary handle with a predetermined force to release the jaw members from the approximated configuration. The latch mechanism may be formed from metal.

The mechanical interface(s) of the latch mechanism may be a latch pin that extends perpendicularly with respect to the generally elongated medial portion of the latch mechanism and the corresponding mechanical interface disposed within the stationary handle may be in the form of a railway. The latch pin may extend from a left or right side of the generally elongated medial portion. Alternatively, the latch pin may extend from left and right sides of the generally elongated medial portion.

The generally elongated medial portion may be tapered at the proximal end of the latch mechanism to facilitate deformation thereof. The generally elongated medial portion may include a notch at the proximal end of the latch mechanism to facilitate deformation thereof. The mechanical interface(s) of the latch mechanism may remain coupled to the proximal end of the latch mechanism when the mechanical interface(s) is/are deformed to un-latch the corresponding mechanical interface disposed within the stationary handle. The predetermined force may range from about 29 ft·lb to about 31 ft·lb.

An aspect of the instant disclosure provides a surgical instrument. The surgical instrument includes a housing. A movable handle is coupled to the housing and is configured to approximate a pair of jaw members of the surgical instrument toward one another. The movable handle is movable to a locked configuration for maintaining the pair of jaw members in an approximated configuration. A latch mechanism includes a distal end that couples to the movable handle and a proximal end that supports at least one mechanical interface configured to releasably engage a corresponding mechanical interface disposed within a stationary handle of the housing. The latch mechanism includes a generally elongated medial portion that extends from the distal end thereof. The at least one mechanical interface of the latch mechanism engages the mechanical interface disposed within the stationary handle to lock and unlock the jaw members in and from the approximated configuration when the movable handle is moved. The at least one mechanical interface being configured to deform and separate from the corresponding mechanical interface disposed within the stationary handle when the movable handle is moved from a jammed position within the stationary handle with a predetermined force to release the movable handle from the locked positioned and the jaw members from the approximated configuration.

BRIEF DESCRIPTION OF THE DRAWINGS

The accompanying drawings, which are incorporated in and constitute a part of this specification, illustrate embodiments of the present disclosure and, together with the detailed description of the embodiments given below, serve to explain the principles of the disclosure.

FIGS. 4A and 4B are perspective views of the latch mechanism shown in FIG. 3 with a pin of the latch shown in pre-deformed and deformed configurations, respectively;

DETAILED DESCRIPTION

Detailed embodiments of the present disclosure are disclosed herein; however, the disclosed embodiments are merely examples of the disclosure, which may be embodied in various forms. Therefore, specific structural and functional details disclosed herein are not to be interpreted as limiting, but merely as a basis for the claims and as a representative basis for teaching one skilled in the art to variously employ the present disclosure in virtually any appropriately detailed structure.

Figure 1:
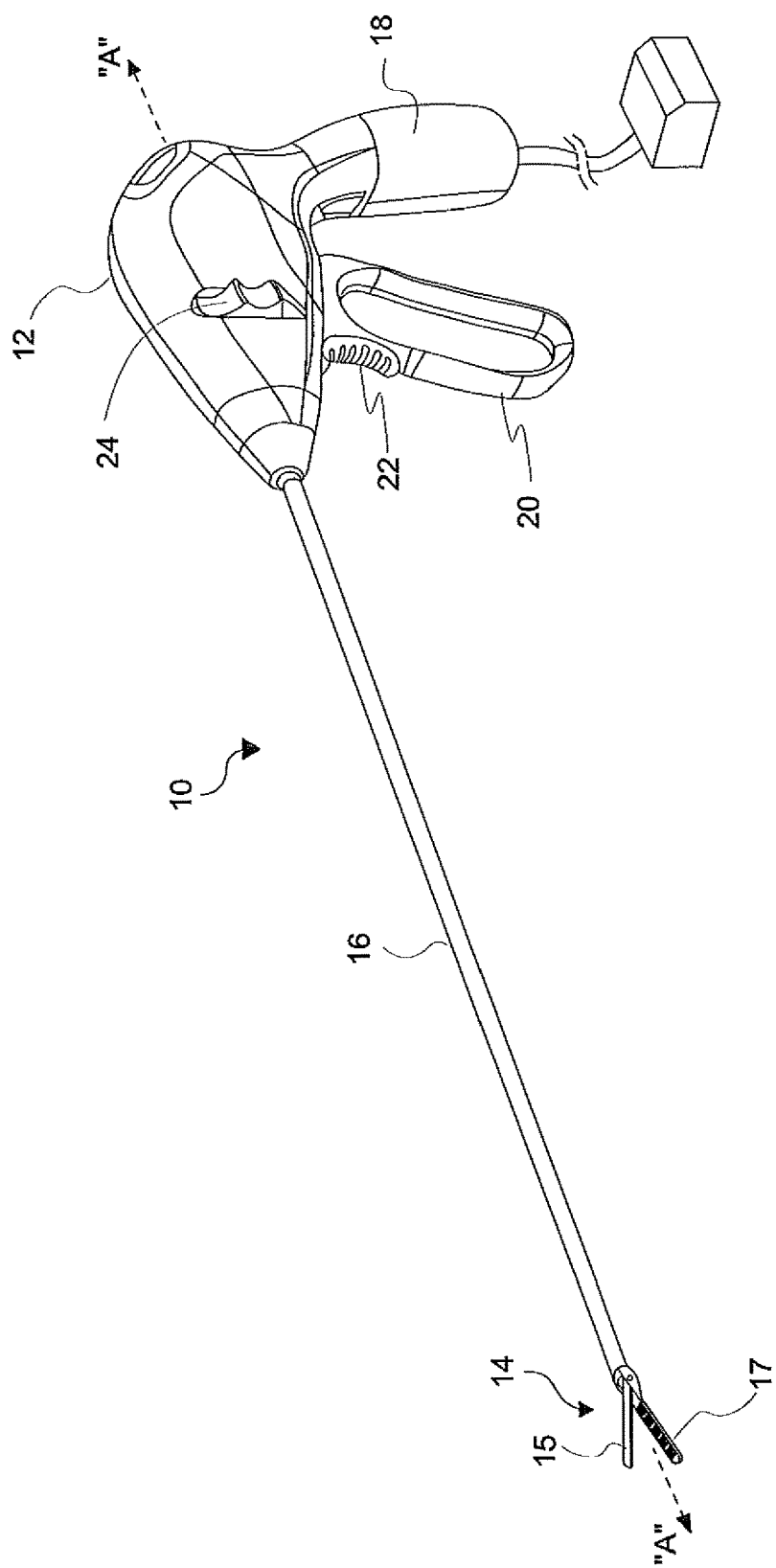
FIG. 1 is a perspective view of an electrosurgical forceps including a latch mechanism according to an embodiment of the present disclosure.
Figure 2:
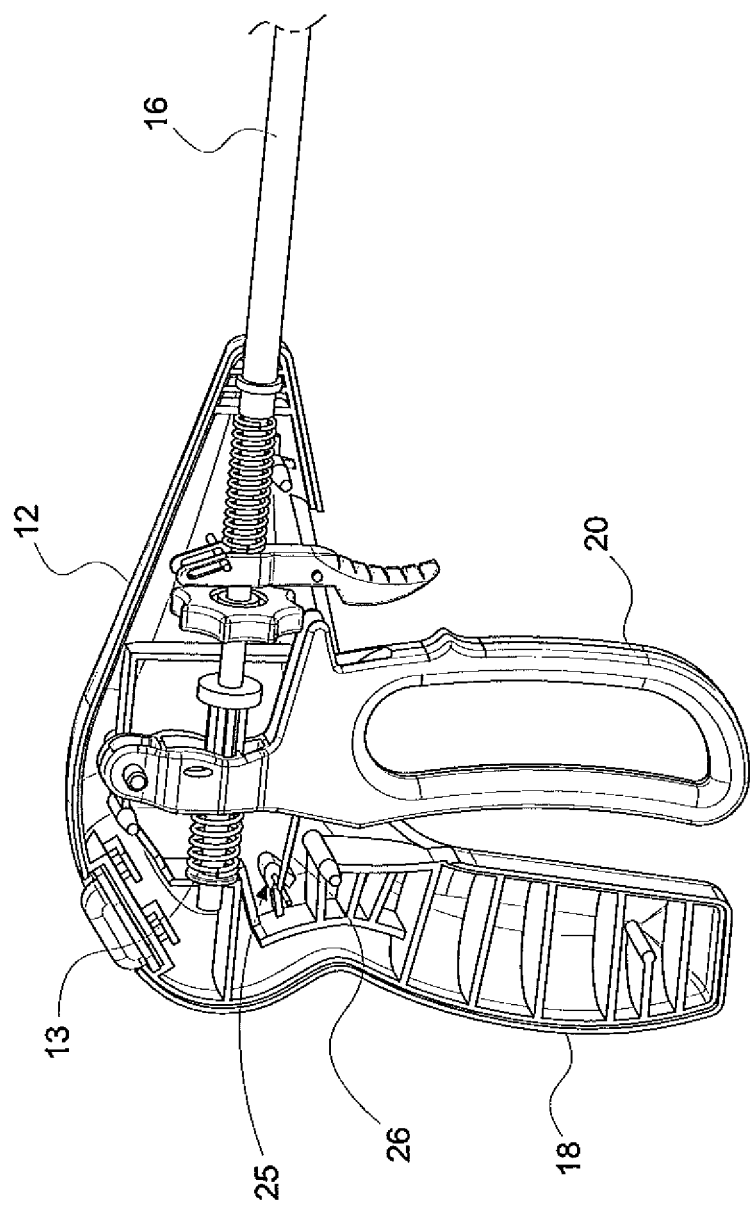
FIG. 2 is a side cut-away view of a proximal end of the electrosurgical forceps shown in FIG. 1.
Figure 3:
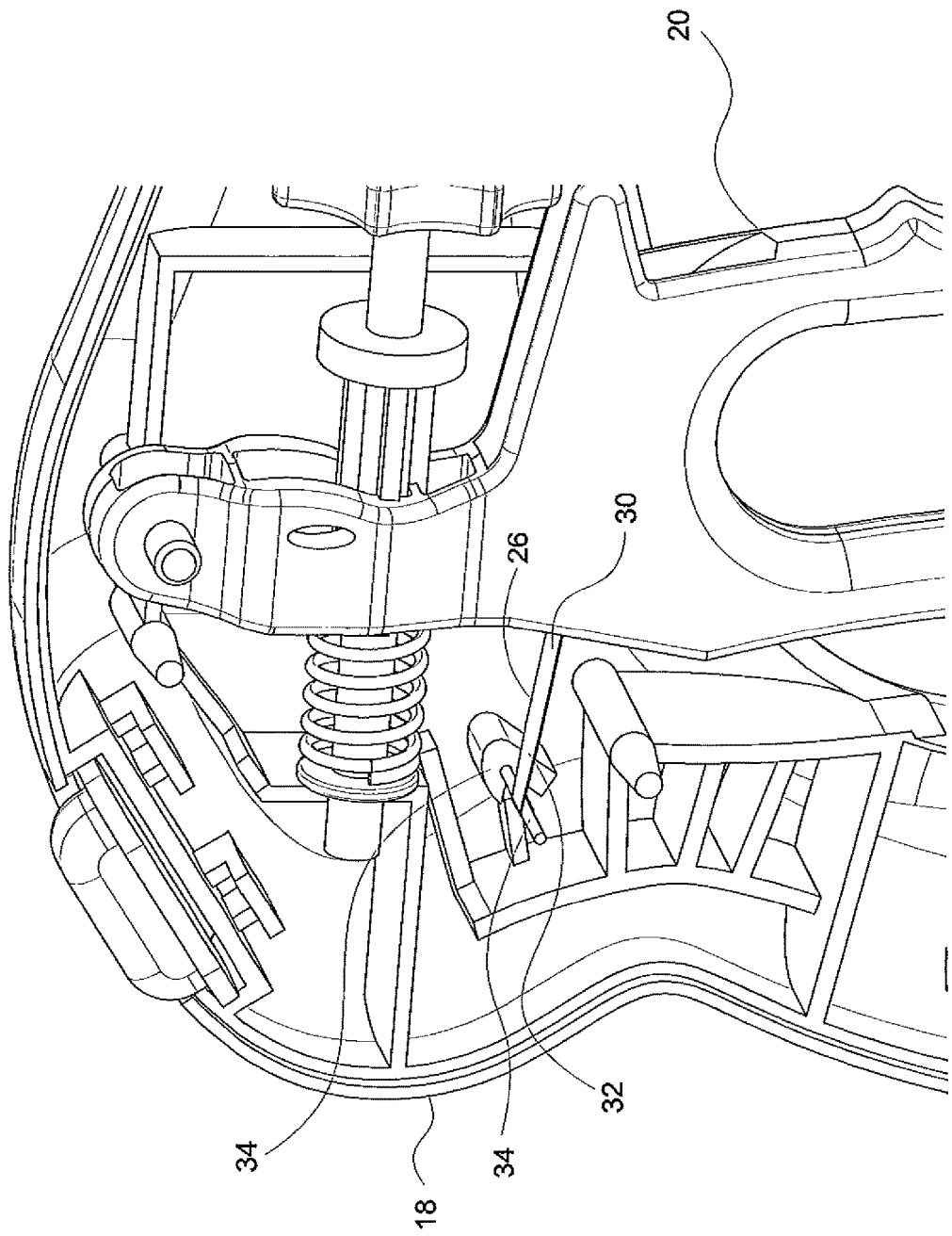
FIG. 3 is a partial, cut-away view of the proximal end of the electrosurgical forceps shown in FIG. 1 with parts removed to illustrate a latch mechanism of a movable handle of the electrosurgical forceps.

Referring initially to FIG. 1, an embodiment of an electrosurgical forceps 10 generally includes a housing 12 that supports various actuators for remotely controlling an end effector 14 through an elongated shaft 16. Although this configuration is typically associated with instruments for use in laparoscopic or endoscopic surgical procedures, various aspects of the present disclosure may be practiced with traditional open instruments and in connection with endoluminal procedures as well.

To mechanically control the end effector 14, the housing 12 supports a stationary handle 18, a movable handle 20, a trigger 22 and a rotation knob 24. The movable handle 20 is operable to move the end effector 14 between an open configuration (FIG. 1) wherein a pair of opposed jaw members 15, 17 are disposed in spaced relation relative to one another, and a closed or clamping configuration (not explicitly shown) wherein the jaw members 15, 17 are closer together. Approximation of the movable handle 20 towards the stationary handle 18 serves to move the end effector 14 to the closed configuration and separation of the movable handle 20 from the stationary handle 18 serves to move the end effector 14 to the open configuration. The movable handle 22 may be moved from the distal position to an intermediate position to move the jaw members 15, 17 to the closed configuration. The movable handle 20 may be moved from the intermediate position to a fully actuated or proximal position to increase the pressure applied by the jaw members 15, 17. When the movable handle 20 is in a fully actuated or proximal position, electrosurgical energy may be selectively supplied to the end effector 14 to effect tissue, e.g., seal tissue.

The trigger 22 is operable to extend and retract a knife blade (not explicitly shown) through the end effector 14 when the end effector 14 is in the closed configuration. The rotation knob 24 serves to rotate the elongated shaft 16 and the end effector 14 about a longitudinal axis A-A extending through the forceps 10. For a more detailed description of the forceps 10, reference is made to U.S. patent application Ser. No. 13/461,355 filed on May 1, 2012 by Allen I V et al.

With reference to FIGS. 2-4B, a latch mechanism 26 according to an embodiment of the instant disclosure is illustrated. The latch mechanism 26 may be formed from any suitable material including without limitation to metal, plastic, etc. In the illustrated embodiment, the latch mechanism 26 is formed from metal.

Latch mechanism 26 includes a distal end 28 (FIG. 4B) that couples to the movable handle 20 and is movable therewith as the movable handle 20 is moved to and from the distal, proximal, and intermediate positions. The distal end 28 may be bent to one or more configurations to function as a latch spring 27 that is configured to bias the movable handle 20 to the distal configuration, see FIG. 4B for example.

A generally elongated medial portion 30 extends from the distal end 28 of the latch mechanism 26. In the embodiment illustrated in FIGS. 1-4B, the elongated medial portion 30 tapers toward the end of the latch mechanism 26 to form the proximal end 32 with a reduced width; the significance of which is described in detail below.

A mechanical interface in the form of a latching pin 34 is supported by the proximal end 32 of the latch mechanism 26 and is configured to releasably engage a corresponding mechanical interface, e.g., a railway 25 (FIGS. 2-3), supported within the stationary handle 18. The railway 25 and latching pin 34 serve to temporarily lock the movable handle 20 in the proximal position against the bias of a compression spring 13 (see FIG. 2 for example). Thus, the railway 25 maintains pressure at the end effector 14 without actively maintaining pressure on the movable handle 20. The latching pin 34 may be released from the railway 25 by pivoting the movable handle 20 proximally and releasing the movable handle 20 to move under the influence of the spring 13. Operation of the railway 25 is described in greater detail in commonly-owned U.S. Pat. No. 7,766,910 to Hixson et al.

Unlike conventional latch mechanisms, the latching pin 34 of the latch mechanism 26 is deformable to separate from the railway 25 disposed within the stationary handle 18 when a predetermined force is exerted on the movable handle 20. In essence, the latching pin 34 serves as a mechanical fuse that is configured to predictably "fail" when a surgeon attempts to force the latch mechanism 26 open after the movable handle 20 has been moved to the locked configuration. Specifically, as a result of the reduced width of the proximal end 32 of the latch mechanism 26, the latching pin 34 deforms, e.g., bends, (FIG. 4B) against the bias of the latch spring 27 at the distal end 28 of the latch mechanism 26 when the surgeon moves the movable handle 20 distally with a predetermined force. As the movable handle 20 is being moved distally with the predetermined force, the latching pin 34 continues to deform until the latching pin 34 separates from the railway 25. Accordingly, if the latching pin 34 were to get jammed, stuck or trapped in the locked configuration, the surgeon could "force" or un-latch the latching pin 34 from the railway 25 to open the jaw members 15, 17 and remove the forceps 10 from the surgical site. As defined herein, the terms jammed, stuck or trapped mean "caught or held in a position so as not being able to move as intended."

In embodiments, such as the illustrated embodiment, the latching pin 34 of the latch mechanism 26 remains coupled to the proximal end 32 of the latch mechanism 26 when the latching pin 34 is deformed to separate from the railway 25 (see FIGS. 4A and 4B for example). Alternatively, in embodiments, the latching pin 34 of the latch mechanism 26 may be configured to uncouple from the proximal end 32 of the latch mechanism 26 when the latching pin 34 is deformed to separate from the railway 25.

Through empirical testing, it has been found that a suitable predetermined force that may be exerted by a user on the movable handle 20 to deform the latching pin 34 (having a diameter that ranges from about 0.145 inches to about 0.155 inches) of the latch mechanism 26 may range from about 29 ft·lb to about 31 ft·lb. In an embodiment, such as the illustrated embodiment, the force exerted by a user on the movable handle 20 to deform the latching pin 34 (having a diameter that is approximately 0.150 inches) of the latch mechanism 26 is approximately equal to 30 ft·lb.

Figure 5:
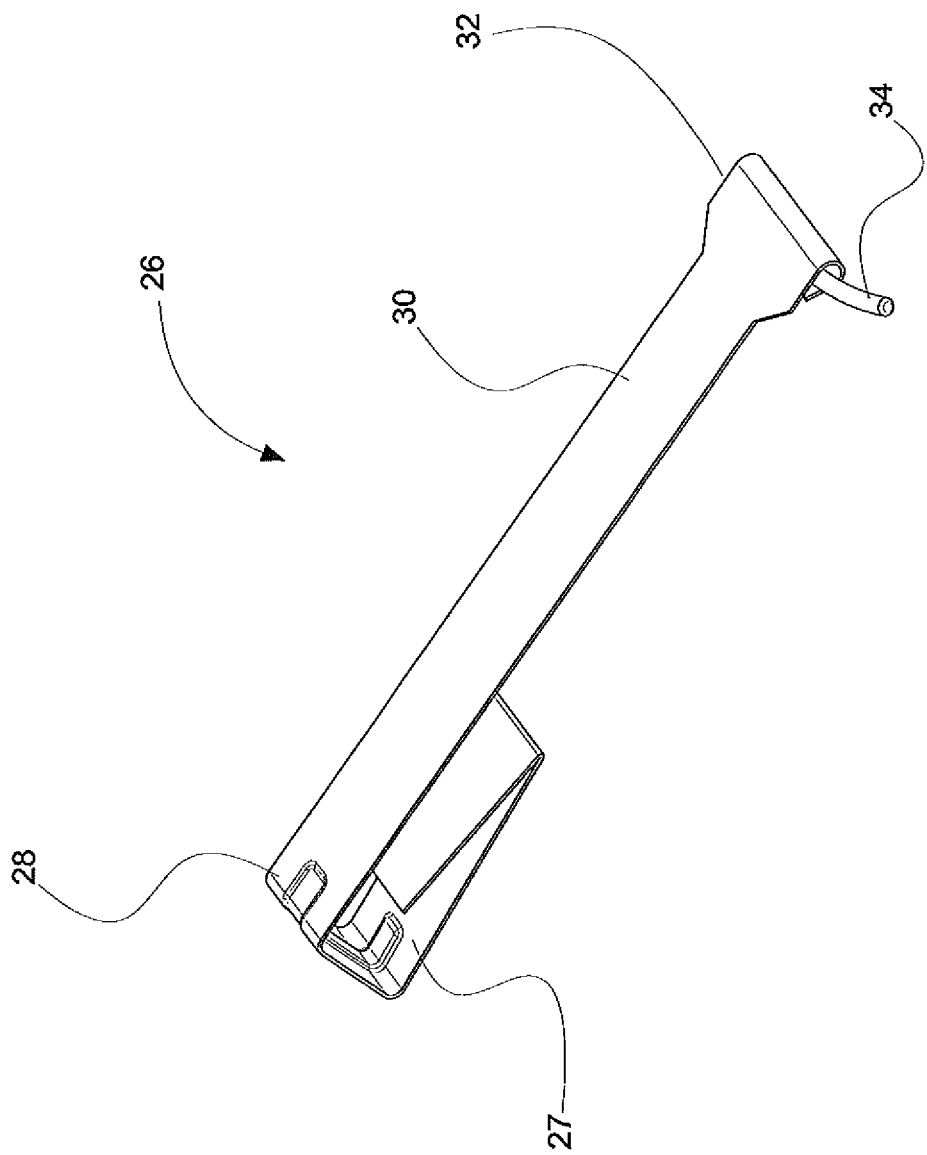
FIG. 5 is a perspective view of a latch mechanism according to another embodiment of the instant disclosure.

Latching pin 34 extends perpendicularly with respect to the elongated medial portion 30 of the latch mechanism 26 to engage the railway 25 and deforms when the aforementioned forces are exerted by a user to move the movable handle 20 distally. In embodiments, the latching pin 34 may extend from left and right sides of the elongated medial portion 30 (FIGS. 4A and 4B). Alternatively, as shown in FIG. 5, the latching pin 34 may extend from one of the left and right sides of the elongated medial portion 30.

In use, movable handle 20 may be moved to the proximal position to move the latching pin 34 into engagement with the railway 25 which locks the jaw members 15, 17 in the approximated configuration. In the event the latching pin 34 gets trapped, jammed or stuck within the railway 25, the unique configuration of the latch mechanism 26 that includes the latching pin 34 allows a user to move the movable handle 20 distally with the aforementioned predetermined forces to separate the latching pin 34 from the railway 25, which, in turn, releases the jaw members 15, 17 from the approximated configuration.

Figure 6:
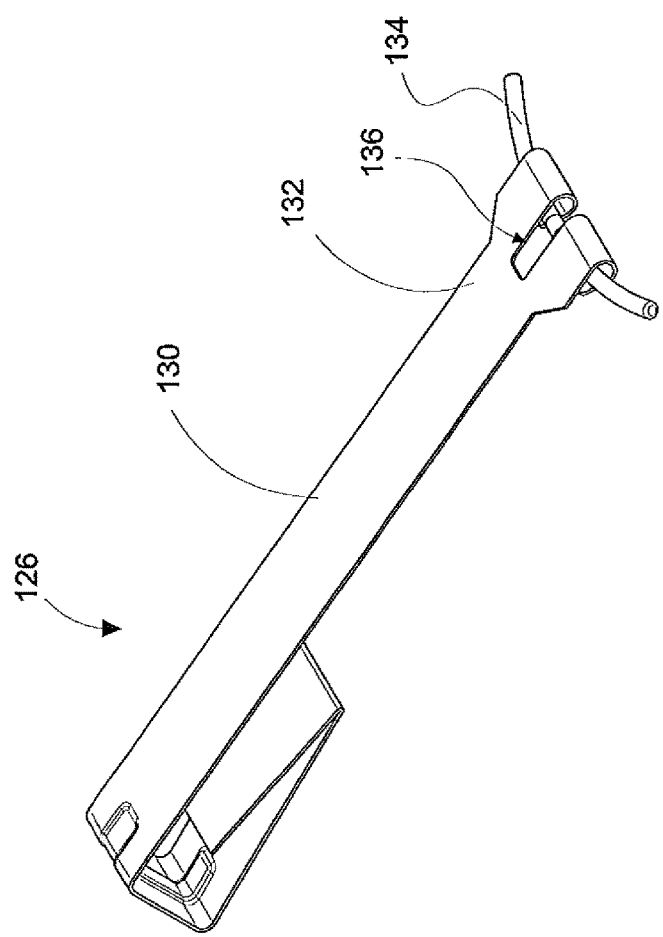
FIG. 6 is a perspective view of a latch mechanism according to yet another embodiment of the instant disclosure.

From the foregoing and with reference to the various figure drawings, those skilled in the art will appreciate that certain modifications can also be made to the present disclosure without departing from the scope of the same. For example, in embodiments, the proximal end 32 may be configured to facilitate deformation of the latching pin 34 as shown in the tapered configurations depicted in FIGS. 4A-5. FIG. 6 illustrates a proximal end 132 of a latch mechanism 126 having a notch 136 defined therein that reduces the structural integrity of the proximal end 132 such that the latching pin 134 deforms when the aforementioned forces are exerted on the movable handle 20.

The various embodiments disclosed herein may also be configured to work with robotic surgical systems and what is commonly referred to as "Telesurgery". Such systems employ various robotic elements to assist the surgeon in the operating theatre and allow remote operation (or partial remote operation) of surgical instrumentation. Various robotic arms, gears, cams, pulleys, electric and mechanical motors, etc. may be employed for this purpose and may be designed with a robotic surgical system to assist the surgeon during the course of an operation or treatment. Such robotic systems may include, remotely steerable systems, automatically flexible surgical systems, remotely flexible surgical systems, remotely articulating surgical systems, wireless surgical systems, modular or selectively configurable remotely operated surgical systems, etc.

The robotic surgical systems may be employed with one or more consoles that are next to the operating theater or located in a remote location. In this instance, one team of surgeons or nurses may prep the patient for surgery and configure the robotic surgical system with one or more of the instruments disclosed herein while another surgeon (or group of surgeons) remotely control the instruments via the robotic surgical system. As can be appreciated, a highly skilled surgeon may perform multiple operations in multiple locations without leaving his/her remote console which can be both economically advantageous and a benefit to the patient or a series of patients.

The robotic arms of the surgical system are typically coupled to a pair of master handles by a controller. The handles can be moved by the surgeon to produce a corresponding movement of the working ends of any type of surgical instrument (e.g., end effectors, graspers, knifes, scissors, etc.) which may complement the use of one or more of the embodiments described herein. The movement of the master handles may be scaled so that the working ends have a corresponding movement that is different, smaller or larger, than the movement performed by the operating hands of the surgeon. The scale factor or gearing ratio may be adjustable so that the operator can control the resolution of the working ends of the surgical instrument(s).

The master handles may include various sensors to provide feedback to the surgeon relating to various tissue parameters or conditions, e.g., tissue resistance due to manipulation, cutting or otherwise treating, pressure by the instrument onto the tissue, tissue temperature, tissue impedance, etc. As can be appreciated, such sensors provide the surgeon with enhanced tactile feedback simulating actual operating conditions. The master handles may also include a variety of different actuators for delicate tissue manipulation or treatment further enhancing the surgeon's ability to mimic actual operating conditions.

While several embodiments of the disclosure have been shown in the drawings, it is not intended that the disclosure be limited thereto, as it is intended that the disclosure be as broad in scope as the art will allow and that the specification be read likewise. Therefore, the above description should not be construed as limiting, but merely as examples of particular embodiments. Those skilled in the art will envision other modifications within the scope and spirit of the claims appended hereto.

What is claimed is:

1. A surgical instrument, comprising:
a housing;
a mechanical housing interface disposed within the housing;
a movable handle coupled to the housing and configured to approximate a pair of jaw members toward and away from one another; and
a latch mechanism operably coupled to the movable handle, the latch mechanism including at least one mechanical interface configured to selectively engage the mechanical housing interface to lock and unlock the jaw members in and from an approximated configuration,
wherein, when the movable handle is in a jammed position, the at least one mechanical interface of the latch mechanism is configured to deform beyond a structural integrity thereof and separate from the mechanical housing interface when the movable handle is moved from the jammed position.

2. The surgical instrument according to claim 1, wherein the latch mechanism includes a distal end that couples to the movable handle, a generally elongated medial portion and a proximal end that supports the at least one mechanical interface of the latch mechanism.

3. The surgical instrument according to claim 2, wherein the at least one mechanical interface of the latch mechanism is a latch pin that extends perpendicularly with respect to the generally elongated medial portion of the latch mechanism, and the mechanical housing interface is in the form of a railway.

4. The surgical instrument according to claim 2, wherein the latch mechanism includes a latch pin that extends from at least one of a left or a right side of the generally elongated medial portion.

5. The surgical instrument according to claim 2, wherein the latch mechanism includes a latch pin that extends from left and right sides of the generally elongated medial portion.

6. The surgical instrument according to claim 2, wherein the generally elongated medial portion is tapered at the proximal end of the latch mechanism to facilitate deformation thereof.

7. The surgical instrument according to claim 2, wherein the generally elongated medial portion includes a notch at the proximal end of the latch mechanism to facilitate deformation thereof.

8. The surgical instrument according to claim 2, wherein the at least one mechanical interface of the latch mechanism remains coupled to the proximal end of the latch mechanism when the at least one mechanical interface is deformed to separate from the mechanical housing interface.

9. The surgical instrument according to claim 1, wherein the at least one mechanical interface of the latch mechanism is configured to deform and separate from the mechanical housing interface when the movable handle is moved distally from the jammed position with a predetermined force ranging from about 29 ft·lb to about 31 ft·lb.

10. The surgical instrument according to claim 1, wherein the latch mechanism is formed from metal.

11. A surgical instrument, comprising:
a housing having a stationary handle;
a mechanical housing interface disposed within the stationary handle;
a movable handle coupled to the housing and configured to approximate a pair of jaw members toward one another when the movable handle is moved proximally; and
a latch mechanism including a distal end that couples to the movable handle and a proximal end that supports at least one mechanical interface configured to releasably engage the mechanical housing interface, the latch mechanism including a generally elongated medial portion that extends from the distal end thereof,
wherein the at least one mechanical interface of the latch mechanism engages the mechanical housing interface to lock and unlock the jaw members in and from an approximated configuration when the movable handle is moved, the at least one mechanical interface being configured to deform beyond a structural integrity thereof and separate from the mechanical housing interface when the movable handle is moved from a jammed position within the stationary handle with a predetermined force to release the jaw members from the approximated configuration.

12. The surgical instrument according to claim 11, wherein the at least one mechanical interface of the latch mechanism is a latch pin that extends perpendicularly with respect to the generally elongated medial portion of the latch mechanism, and wherein the mechanical housing interface is in the form of a railway.

13. The surgical instrument according to claim 12, wherein the latch pin extends from at least one of a left and right side of the generally elongated medial portion.

14. The surgical instrument according to claim 12, wherein the latch pin extends from left and right sides of the generally elongated medial portion.

15. The surgical instrument according to claim 11, wherein the generally elongated medial portion is tapered at the proximal end of the latch mechanism to facilitate deformation thereof.

16. The surgical instrument according to claim 11, wherein the generally elongated medial portion includes a notch at the proximal end of the latch mechanism to facilitate deformation thereof.

17. The surgical instrument according to claim 11, wherein the at least one mechanical interface of the latch mechanism remains coupled to the proximal end of the latch mechanism when the at least one mechanical interface of the latch mechanism is deformed to un-latch the mechanical housing interface.

18. The surgical instrument according to claim 11, wherein the predetermined force ranges from about 29 ft·lb to about 31 ft·lb.

19. The surgical instrument according to claim 11, wherein the latch mechanism is formed from metal.

20. A surgical instrument, comprising:
a housing having a stationary handle;
a mechanical housing interface disposed within the stationary handle;
a movable handle coupled to the housing and configured to approximate a pair of jaw members toward one another, the movable handle movable to a locked configuration for maintaining the pair of jaw members in an approximated configuration; and a latch mechanism including a distal end that couples to the movable handle and a proximal end that supports at least one mechanical interface configured to releasably engage the mechanical housing interface, the latch mechanism including a generally elongated medial portion that extends from the distal end thereof, wherein the at least one mechanical interface of the latch mechanism engages the mechanical housing interface to lock and unlock the jaw members in and from the approximated configuration when the movable handle is moved, the at least one mechanical interface of the latch mechanism being configured to deform beyond a structural integrity thereof and separate from the mechanical housing interface when the movable handle is moved from a jammed position within the stationary handle with a predetermined force to release the movable handle from the locked positioned and the jaw members from the approximated configuration.

* * * * *